US012564442B2

(12) United States Patent
Eckert et al.

(10) Patent No.: US 12,564,442 B2
(45) Date of Patent: *Mar. 3, 2026

(54) NON-THERMAL PLASMA GENERATOR FOR DETECTION AND TREATMENT OF MALADIES

(71) Applicant: IOLERA HOLDINGS PTE. LTD., Parkview Square (SG)

(72) Inventors: Bradley N. Eckert, Chandler, AZ (US); Bryon K. Eckert, Chandler, AZ (US); Huan Truong, Chandler, AZ (US)

( * ) Notice: Subject to any disclaimer, the term of this patent is extended or adjusted under 35 U.S.C. 154(b) by 1151 days.

This patent is subject to a terminal disclaimer.

(21) Appl. No.: 17/521,715

(22) Filed: Nov. 8, 2021

(65) Prior Publication Data

US 2022/0061916 A1 Mar. 3, 2022

Related U.S. Application Data

(63) Continuation of application No. 16/950,877, filed on Nov. 17, 2020, now Pat. No. 11,166,762, which is a
(Continued)

(51) Int. Cl.
*A61B 18/18* (2006.01)
*A61B 5/00* (2006.01)
(Continued)

(52) U.S. Cl.
CPC ................ *A61B 18/18* (2013.01); *A61B 5/72* (2013.01); *A61B 5/725* (2013.01); *A61B 5/7475* (2013.01);
(Continued)

(58) Field of Classification Search
CPC .... A61L 2/14; A62D 3/10; A62D 3/19; A61B 18/18; A61B 5/7475; A61B 5/0507;
(Continued)

(56) References Cited

U.S. PATENT DOCUMENTS

| | | | |
|---|---|---|---|
| 4,357,709 A | 11/1982 | Butler et al. | |
| 5,115,168 A | 5/1992 | Shoda et al. | |

(Continued)

OTHER PUBLICATIONS

Arata Y., et al., "Contribution of Higher Harmonic Resonance on the Production of ECR Mirror Plasma by 60 GHz Gyrotron," Japanese Journal of Applied Physics, Feb. 1989, vol. 28(2), pp. 234-239.
(Continued)

*Primary Examiner* — Rex R Holmes
(74) *Attorney, Agent, or Firm* — Messner Reeves LLP; Scott J. Hawranek

(57) ABSTRACT

A single non-thermal atmospheric plasma generation device is used to detect and analyze vital fields of a living subject to determine the presence of a condition, such as an illness or injury, and responsively modify characteristics of the plasma to treat, heal, or alleviate the condition. The device includes a capacitance dielectric discharge array of plasma emitters, and a controller having a power supply, a transformer, and circuit components for driving the transformer at a resonant frequency of the plasma emitters to cause the plurality of plasma emitters to ionize surrounding air and produce the non-thermal plasma. The resonant frequency is around 60 GHz and harmonics thereof. A receiver of the device recovers frequency mixing products from the plasma, which are extracted by signal processing circuitry; signals in the VHF and UHF bands are extracted and analyzed to determine whether signatures of particular vital fields are present.

20 Claims, 4 Drawing Sheets

Related U.S. Application Data continuation-in-part of application No. PCT/US2020/031725, filed on May 6, 2020, and a continuation-in-part of application No. 15/636,554, filed on Jun. 28, 2017, now Pat. No. 11,432,732.

(60) Provisional application No. 62/843,978, filed on May 6, 2019, provisional application No. 62/355,537, filed on Jun. 28, 2016.

(51) Int. Cl.
| | |
|---|---|
| *H05H 1/24* | (2006.01) |
| *A61B 5/0507* | (2021.01) |
| *A61B 18/00* | (2006.01) |

(52) U.S. Cl.
CPC ......... *H05H 1/2406* (2013.01); *A61B 5/0507* (2013.01); *A61B 2018/0016* (2013.01); *A61B 2018/00642* (2013.01); *A61B 2018/00696* (2013.01); *H05H 2240/20* (2013.01); *H05H 2245/30* (2021.05); *H05H 2245/32* (2021.05); *H05H 2245/34* (2021.05)

(58) Field of Classification Search
CPC ......... A61B 5/72; A61B 5/7257; A61B 5/725; A61B 2562/0228; A61B 2018/00642; A61B 2018/0016; A61B 2018/00696; H05H 1/2406; H05H 2001/2412; H05H 2245/122; G01R 29/0814; G01R 29/0892
See application file for complete search history.

(56) References Cited

U.S. PATENT DOCUMENTS

| | | | |
|---|---|---|---|
| 5,130,003 | A | 7/1992 | Conrad |
| 5,363,054 | A | 11/1994 | Bekefi |
| 5,705,931 | A | 1/1998 | Klick |
| 5,909,086 | A | 6/1999 | Kim et al. |
| 6,347,238 | B1 | 2/2002 | Levengood et al. |
| 6,713,965 | B2 | 3/2004 | Jang et al. |
| 7,564,419 | B1 | 7/2009 | Patel |
| 8,460,283 | B1 | 6/2013 | Laroussi et al. |
| 2004/0135590 | A1 | 7/2004 | Quon |
| 2005/0116871 | A1 | 6/2005 | Moheb et al. |
| 2008/0097183 | A1 | 4/2008 | Monro |
| 2009/0292196 | A1 | 11/2009 | Eckert et al. |
| 2010/0296977 | A1 | 11/2010 | Hancock |
| 2011/0109519 | A1 | 5/2011 | Quan et al. |
| 2011/0118556 | A1 | 5/2011 | Siegel et al. |
| 2012/0156093 | A1 | 6/2012 | Kitano |
| 2012/0309328 | A1 | 12/2012 | Morrison et al. |
| 2013/0253302 | A1 | 9/2013 | Eckert et al. |
| 2014/0088433 | A1 | 3/2014 | Shan |
| 2014/0263202 | A1 | 9/2014 | Partridge |
| 2014/0309522 | A1 | 10/2014 | Fullerton et al. |
| 2014/0319382 | A1 | 10/2014 | Hancock et al. |
| 2015/0056107 | A1 | 2/2015 | Hancock |
| 2016/0065256 | A1 | 3/2016 | Yun et al. |
| 2016/0317061 | A1 | 11/2016 | Ostadrahimi et al. |
| 2016/0337986 | A1 | 11/2016 | Broda et al. |
| 2016/0372310 | A1 | 12/2016 | Chung et al. |
| 2017/0367613 | A1 | 12/2017 | Eckert et al. |
| 2021/0068896 | A1 | 3/2021 | Eckert et al. |

OTHER PUBLICATIONS

Ibrahim M., et al., "Performance Analysis of Fast Fourier Transform on Field Programmable Gate Arrays and Graphic Cards," 2016, 5 pages.

International Search Report and Written Opinion issued in International Application No. PCTUS2020031725, mailed on Jul. 22, 2020, 6 pages.

Jackson G.L., et al., "Second Harmonic Electron Cyclotron Pre-Ionization in the DIII-D Tokamak," Nuclear Fusion, Mar. 19, 2007, vol. 47, pp. 257-263.

Kamoda H., et al., "Millimeter-Wave Beam Former Using Liquid Crystal," 34th European Microwave Conference, 2004, pp. 1141-1144.

Nie Q Y., et al., "A Two-Dimensional Cold Atmospheric Plasma Jet Array for Uniform Treatment of Large-Area Surfaces for Plasma Medicine," New Journal of Physics, 2009, vol. 11, 15 pages.

Rubinski D., "Incremental Encoder Ouput Signal Overview," Wayback Machine Document, 2015, 1 page.

Sathasivam S., et al., "ASIC Implementation of High throughout FFT Processorfor Scientific Applications," 2016, 5 pages.

Schmuck S., et al., "Electron Cyclotron Emission Spectra in X- and O-Mode Polarisation at JET: Martin-Puplett Interferometer, Absolute Calibration, Revised Uncertainties, Inboard/Outboard Temperature Profile, and Wall Properties," Review of Scientific Instruments, 2016, vol. 87(9), pp. 1-25.

Udintsev., V.S., et al., "New ECE Diagnostics forthe TEXTOR-94 Tokamak," Review of Scientific Instruments, Jan. 3, 2001, vol. 72 (1), pp. 359-362.

Wiltse J.C., "History of Millimeter and Submillimeter Waves," IEEE Transactions on Microwave Theory and Techniques, Sep. 9, 1984, vol. 32 (9), 10 pages.

Yang Z., et al., "Vital Sign and Sleep Monitoring Using Millimeter Wave", ACM Transactions on Sensor Networks, Apr. 30, 2017, Retrieved from the Internet: https://dl.aom.org/doi/pdf/10.1145/3051124https://dl.acm.org/doi/pdf/10.1145/3051124./url:>.

NON-THERMAL PLASMA GENERATOR FOR DETECTION AND TREATMENT OF MALADIES

CROSS-REFERENCE TO RELATED APPLICATIONS

This application is a continuation of U.S. patent application Ser. No. 16/950,877, filed Nov. 17, 2020 under the title "Non-Thermal Plasma Generator for Detection and Treatment of Maladies" which is a continuation-in-part of, and claims the benefits of priority under 35 U.S.C. 120 and 35 U.S.C. 365(c) from, Int'l. Pat. App. Ser. No. PCT/US2020/031725, filed May 6, 2020, under the title "Putative Energy Field Analysis Using Non-Thermal Plasma Array," which claims the benefit of priority from U.S. Prov. Pat. App. Ser. No. 62/843,978, filed May 6, 2019, under the same title, both of which patent applications are incorporated fully herein by reference, and this application is a continuation-in-part of, and claims the benefit of priority from, U.S. patent application Ser. No. 15/636,554, filed Jun. 28, 2017, under the title "SYSTEM AND METHOD OF MEASURING MIL-LIMETER WAVE OF COLD ATMOSPHERIC PRESSURE PLASMA," which claims priority from U.S. Prov. Pat. App. Ser. No. 62/355,537, filed Jun. 28, 2016, under the title "METHOD OF MEASURING MILLIMETER WAVE OF COLD ATMOSPHERIC PLASMA ARRAY," both of which patent applications are incorporated fully herein by reference, and this application incorporates fully herein by reference the entirety of each of the following related patent applications: U.S. Prov. Pat. App. Ser. No. 62/247,265, filed Oct. 28, 2015, and Int'l. Pat. App. Ser. No. PCT/US2016/069011, filed Dec. 28, 2016, and U.S. 371 App. Ser. No. 15/772,318, filed Apr. 30, 2018, and pending U.S. patent application Ser. No. 16/937,577, filed Jul. 23, 2020, each entitled "Methods of Cross Correlation of Biofield Scans to Enome Database, Genome Databases, Blood Tests and Phenotype Data;" U.S. Prov. Pat. App. Ser. No. 62/235,517, filed Sep. 30, 2015, under the title "Devices and Methods for Creating Non-Thermal Plasma and Ozone," and U.S. patent application Ser. No. 15/055,028, filed Feb. 26, 2016, under the title "Devices for Creating Non-Thermal Plasma and Ozone," now U.S. Pat. No. 9,572,241; U.S. patent application Ser. No. 15/213,201, filed Jul. 18, 2016, now U.S. Pat. No. 9,826,618, and U.S. patent application Ser. No. 15/787,603, filed Oct. 18, 2017, now U.S. Pat. No. 10,165,666, and U.S. patent application Ser. No. 16/233,004, filed Dec. 26, 2018, now U.S. Pat. No. 10,681,798, and pending U.S. patent application Ser. No. 16/896,136, filed Jun. 8, 2020, each under the title "Devices for Controlling Non-Thermal Plasma Emitters;" and, U.S. Prov. Pat. App. Ser. No. 63/007,931, filed Apr. 9, 2020, under the title "Treatment of Infectious Diseases with Non-Thermal Plasma."

FIELD OF INVENTION

This disclosure relates to energy field detection, pattern analysis, and non-invasive healing and therapy using non-thermal plasma. In particular it relates to methods and devices for generating non-thermal atmospheric-pressure plasma, detecting interactions of the plasma with energy fields emitted by organisms, analyzing the energy fields based on the detected interactions, and modifying the generation to impart therapeutic characteristics upon the plasma.

BACKGROUND

All live organisms emit energy fields, referred to herein as vital fields, which are characterized by the organic processes that produce or modify them. There is a significant amount of skepticism surrounding vital fields because no known scientific instruments can detect them. The inability to detect, measure, and describe the energy in a vital field is a problem that inhibits human understanding of biological interactions with the environment.

A wave in an energy field is considered to be composed of electric, magnetic, gravitational and temporal components. The electric, magnetic, and gravitational components are orthogonal to each other. In an electromagnetic wave, the gravitational and temporal components have a static value, and the electric and magnetic components vary inversely. In this context, a static temporal component equates to time moving forward at a constant rate. In contrast, a vital wave is theorized to contain static electric and magnetic components and dynamic temporal and gravitational components. Such a wave is essentially a longitudinal or compression wave in the space-time fabric, but is often referred to as a torsion wave. Because vital waves do not have a dynamic magnetic component, they do not induce a current in a conductor. Most known devices rely on such induction and are therefore unable to reliably detect the presence of vital waves or measure or describe them scientifically.

Kirlian photography, discovered in the early 20th century, can be considered one of the earliest means of analyzing vital fields. Kirlian photography works by driving a photographic plate at high voltage, with a biological specimen resting on the plate. The resulting image left on the film is consistent with the corona discharge pattern of the specimen. Live specimens tend to show a shimmering coronal effect, whereas dead specimens and inanimate objects exhibit a more uniform pattern. The difference is attributed to the live specimen having at least one vital field. It should be noted, however, that Kirlian photography as an indicator of vital fields has been met with skepticism, with the results explained away as errors in the experimental process.

Plasmas are a fourth possible state of matter, the others being solid, liquid, and gas. Plasmas are formed when a gas is subjected to high stresses that create a mixture of neutral atoms, positively charged atomic and molecular ions, and freed electrons. There are two types of plasma: thermal, and non-thermal or "cold" plasma. Thermal plasmas are in thermal equilibrium, i.e., the electrons and the heavy particles are at the same temperature. Current technologies create thermal plasma by heating gas or subjecting the gas to a strong electromagnetic field applied with a generator. As energy is applied with heat or electromagnetic field, the number of electrons can either decrease or increase, creating positively or negatively charged particles called ions. Thermal plasma can be produced by plasma torches or in high-pressure discharges. If thermal plasma is used in treating a material or surface sensitive to heat, it can cause significant thermal desiccation, burning, scarring and other damage.

In order to mitigate such damage, methods and devices have been created for applying non-thermal plasma to heat-sensitive materials and surfaces. Whereas in thermal plasmas the heavy particles and electrons are in thermal equilibrium with each other, in non-thermal plasmas the electrons are much more energetic than the neutral or positively charged particles; the positive ions and neutrals are therefore at a much lower temperature (sometimes as low as room temperature) than the electrons. Non-thermal plasma usually can operate at less than 104° F. at the point of contact. Thus non-thermal plasmas are not likely to damage human tissue. The application of non-thermal plasma in medicine has recently been a fruitful field of research. The beneficial health effects of non-thermal plasma applications in living organisms are often attributed to reactive oxygen or nitrogen species. Closer investigation of the health effects imparted by an array of micro-plasmas placed near the skin shows energetic effects that are not explained by conventional science. If these energetic effects can be electronically analyzed in real time, the information can be used to provide feedback to the user to show the optimum application of plasma to the body, the progress of healing, and the amount of pain.

SUMMARY

The present device is a putative energy field analyzer that detects energy fields converted to electromagnetic energy by a plasma emitter array. The plasma emitter array can be a dielectric barrier discharge array fabricated on a thin substrate with low dielectric loss. This can be FR-4, PEEK, a cyclic olefin fiberglass laminate, or other similar low-loss material. The oxygen plasma will erode the polymer over time, but the array lifetime can be extended with a thin film of oxide, typically aluminum oxide deposited by atomic layer deposition.

An applied AC voltage causes breakdown of the surrounding air in the sub-nanosecond range. The array is typically covered by an air permeable, electrically insulating sheet and placed next to the skin. The velocity of the plasma away from the electrodes is inversely proportional to the size of the plasma discharge. In the case of the micro-plasma, it is sufficiently high to cause relativistic effects. This converts the torsion waves of the vital field emanating from the body to electromagnetic waves that are conducted through the plasma array.

The array of plasma plumes provides a large number of mutually coupled areas of population inversion. This is caused by the collapsing non-linear magnetic field during the plasma discharge. The polar nature of the oxygen molecule causes a large number of hyperfine resonant frequencies from 53 GHz to 2.5 THz and beyond. At these frequencies, amplification by stimulated emission can take place.

Because each plasma plume discharges at a slightly different time, spontaneous emission from the array will manifest as broadband noise. However, a biological specimen will generate a large number of modulated carriers close to the hyperfine resonant frequencies of oxygen. These carriers are not detectable with normal millimeter-wave electronics, since there is no dynamic magnetic component in the torsion waves that comprise the vital energy field.

In operation, the plasma array is held between 2 and 10 mm from the surface of the patient's skin. The plasma produces therapeutic effects without contacting the skin or passing current through the body. When the array is placed close to the skin, the plasma plumes convert this energy to electromagnetic waves that might be detected by extremely sensitive millimeter-wave electronics, but the cost is very high and this approach is not suited to a consumer device intended for broad usage. However, the present system's consumable array is low-cost and runs at a low enough voltage to allow economical construction of a mobile system.

DETAILED DESCRIPTION

At least through incorporation by reference of the patent applications and patents identified above, the present disclosure includes extensive description of the inventors' previous developments of non-thermal plasma generating devices and methods of using such devices, including detection and characterization of putative energy, or "vital," fields, and treatment of human subjects with characterized plasma to resolve maladies, including without limitation toe fungus, wounds, wound infections, presence of infectious agents and pathogens, etc. Cold Atmospheric Plasma (CAP) has shown great effectiveness as a healing technology. In addition, modulation of the plasma at specific frequencies, as described herein and in the inventors' previous work, enhances the healing effects, often breaking up biofilms under the skin to allow the body to rapidly heal seemingly intractable infections. For example, microwave frequency effects of the non-thermal plasma can be exploited to energize the vital field(s) of a subject.

Extremely high-frequency (EHF) therapy is the practice of using low-intensity electromagnetic radiation in the millimeter band for the treatment of internal disorders, such as various types of cancer and tumors. Recently a possible link between the fine resonance frequencies of oxygen in the 60 GHz region and the therapeutic frequencies used in non-thermal EHF therapy has been investigated. This link could be characteristic of biological torsion fields, and as described in the present disclosure, the inventors are building upon this link to further harness the therapeutic mechanisms of plasma medicine.

The inventors' previous and present work further suggest that an unexplained repulsive force that is occasionally observed during non-thermal plasma treatment of infections may point the way to an efficient mechanism for characterizing biofield energy. Ambient pressure air plasma in non-thermal equilibrium creates localized areas where a population of atoms or molecules are induced to a higher state of excitability, known as population inversion, causing spontaneous emission at magnetic dipole rotational resonance lines. For $O_2$, many of these lines occur in the 60 GHz frequency range. The conversion process between torsion wave vital energy and electromagnetic energy through plasma interaction is a non-linear process. This creates mixing products between the carriers, some of which can be analyzed in the VHF and UHF frequency ranges. To help reject radio signals, these signals are analyzed by narrowband spectrum analysis.

Figure 1:
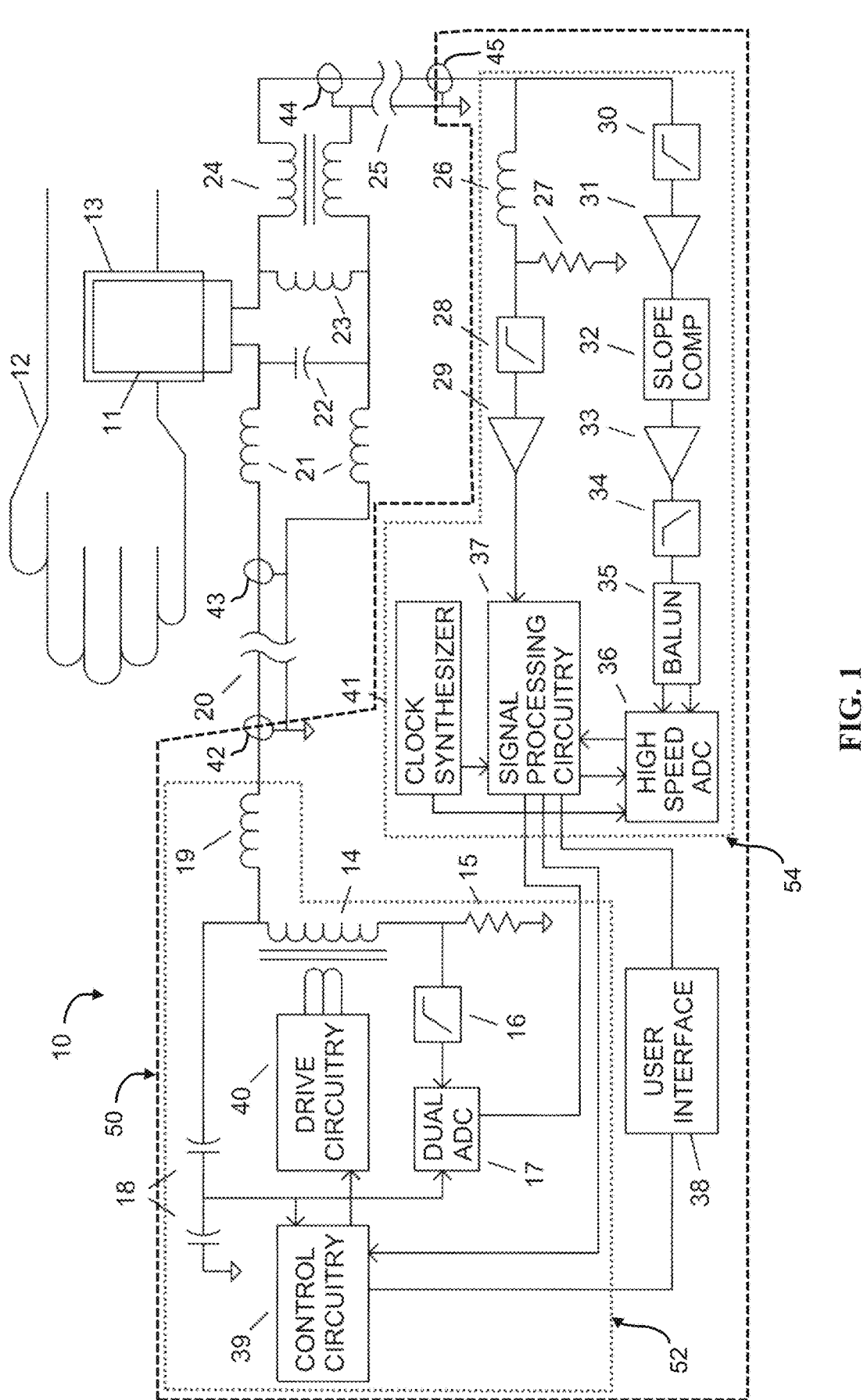
FIG. 1 is a schematic diagram of an example putative energy field analyzer in accordance with the disclosure.

FIG. 1 illustrates an example embodiment of the presently described system 10 for detecting and treating maladies using non-thermal plasma, and an example method of use. The system 10 ionizes atmosphere to produce a non-thermal plasma having particular propagation characteristics, such as intensity, plasma discharge frequency, and modulation frequency. The plasma is generated at an array 11 of plasma emitters, which is electrically connected to control circuitry 39 and/or drive circuitry 40 as described further herein. The array 11 may be electrically insulated by an air-permeable sheet or pouch 13 that contacts the skin 12 of a subject, preventing electric shock to the subject and allowing the array to be disposed approximate (e.g., 2-10 mm from) the surface of the skin 12. The array 11 is driven by high voltage transformer 14, through high frequency filter inductor 19 to a shielded array cable 20. Cable 20 connects the plasma driver to the array. Inductors 21 isolate high frequency currents generated by the plasma from the array cable 20, reducing electromagnetic interference (EMI).

Capacitor 22 provides a path for high frequency current through the array 11, which current goes through coupled inductor 24. This coupled inductor 24 isolates common mode high frequency currents from the shield of the attached coaxial cable 25, reducing EMI. However, coupled inductor 24 allows the differential mode current generated across inductor 23 to flow through the center conductor of cable 25. Cable 25 may in some embodiments be a separate cable from cable 20, connected between the array and a signal processing side of the circuitry in the controller, and carrying only the high frequency signals from the array as sensed by inductor 23. Inductor 23 provides a current return at the plasma drive frequency while maintaining a high impedance in the VHF and UHF frequency range. Inductor 26 is typically the same value as inductor 23, and provides a low impedance connection to cable terminating resistor 27 at frequencies in the HF range. High pass filter 28 is typically a multipole RC filter to provide an optimum pulse response for plasma discharge detection. The pulse signal is converted to logic level with voltage comparator 29.

High pass filter 30 is typically a five element LC filter with 60 MHz cutoff frequency. This rejects harmonics of the plasma drive while passing the plasma frequency mixing signals from the $O_2$ hyperfine resonances from 75 to 1500 MHz. Amplifier 31 is typically a pair of amplifiers to get high gain, low noise figure and high output level. A slope compensation circuit 32 is added to reduce gain by typically 20 dB at low frequencies. This compensates for the high frequency rolloff of the array and amplifier. Amplifier 33 can be a wideband amplifier to reduce the system noise figure. Low pass filter 34 is typically a five element LC filter with cutoff at 1500 MHz. This feeds balun 35, which converts the unbalanced input signal into a balanced signal that then is used to drive a high speed analog to digital converter (ADC) 36. The sample data width should be at least 10 bits. The ADC sample rate is $2^{16}$ times the plasma frequency, typically between 3.6 GSPS and 6 GSPS. All data converters in the system and the plasma drive are synchronized to clock synthesizer 41, which may be a sigma-delta fractional-N synthesizer or similar, in various embodiments. This runs between 3.6 and 6 GHz, and is divided by 65536 to get the plasma drive frequency, and divided by 256 to clock the power measurement ADC 17. A fractional dither factor is used to divide the plasma frequency to get a particular plasma modulation frequency.

Signal processing circuitry 37 begins collecting data during either the positive or negative plasma discharge pulse, during the plasma-on period of the modulation cycle. The discharge pulse width is typically 200 ns, with a period between 11 and 18 us or duty cycle between 1.1% and 1.8%. The low duty cycle helps differentiate between plasma signals and radio interference. A window function is applied to the data over the 200 ns window to reduce radio interference. The data (typically 720 to 1200 samples) is then processed with a $2^{16}$ complex FFT. The FFT result is the same as the plasma frequency. A typical system 10 should have around 64 useful FFT results, and the rest are discarded. The complex phase of each subsequent FFT result is rotated by an appropriate angle to shift each IF frequency to about one fifth of the plasma modulation frequency. For instance, if the modulation frequency were 1550 Hz, the IF frequency should be 310 Hz. The FFT result is then fractional decimated and low pass filtered to change the sample rate from the plasma frequency to the plasma modulation frequency. Signal analysis is performed at the 310 Hz IF frequency for each of the 64 plasma signals, and appropriate results sent to a display and/or storage.

Each torsion wave signal is expected to be modulated in the frequency range of 1 to 100 Hz, with a frequency chirp approaching the center frequency from either the high or low side. The IF signals obtained from the rotated and decimated FFT results can be further analyzed by using a numerically controlled oscillator (NCO) at 310 Hz to get decimated quadrature baseband signals. The quadrature signals are converted to upper and lower sideband baseband signals. A warp transform is used to search for frequency chirps, and includes decision feedback to acquire and lock the NCO. The chirp data may be analyzed to determine correlation to medical conditions, acupuncture meridians, pain and other parameters. Since a relatively small number of signal peaks are needed for data analysis, the data can be analyzed on the ASIC, or streamed over a USB or wireless connection. The drive circuitry 40 provides a primary drive for high voltage transformer 14. The control circuitry 39 provides power control and fault protection in case of array failure. In an example embodiment, the resonant frequency of the transformer and array combination is measured by the controller in a calibration routine. This may allow a faster shutdown in case of array failure or detection of array contamination. An alternative embodiment may use a self-oscillating transformer primary drive.

In this configuration, a low inductance is needed to overcome the capacitance of the array in order to drive it at high frequency. Due to the relatively small number of turns in the transformer, which carry the induced magnetic flux, the flux density in the ferrite core will be high. A high flux density causes high power dissipation in the core. In some embodiments this may be mitigated by modulating the AC voltage to reduce the average power dissipation, for example at a duty cycle of 30% or 75%.

In one embodiment, average power into the array can be measured by measuring the array current through sense resistor 15. The resulting voltage will largely be the displacement current through the array capacitance. This is reduced by a multi-pole high pass RC filter 16. The array voltage is sampled with capacitive voltage divider 18. The resistors and capacitors in voltage divider 18 and high pass filter 16 should be tight tolerance to reduce measurement error. Voltage and current are sampled by dual analog to digital converter (ADC) 17. The sample rate is typically 256 times the plasma frequency. The signal processing circuitry 37 performs 256 sample FFTs, and computes the complex power for each harmonic of the plasma waveform. The real power in each harmonic are summed, and weighted according to the response of the high pass filter. Real power to the array is then computed on a cycle-by-cycle basis.

In one embodiment, the modulation frequency may typically be set between 200 Hz and 5 kHz. Modulation frequency-dependent energetic effects have been demonstrated in-vitro and in-vivo by numerous researchers in plasma medicine. In a preferred embodiment, the plasma modulation dictates a relatively narrow analysis bandwidth of about 100 Hz. In a preferred embodiment, the high speed ADC 36, fractional-N clock synthesizer 41, signal processing circuitry 37, power measurement dual ADC 17, and control circuitry 39 are implemented in an ASIC. A user interface 38, or a portion thereof, can also be implemented in the ASIC, and/or the user interface 38 can include stand-alone components. For example, the user interface 38 may include a display screen for displaying operating parameters, detection results, and navigational menus for selecting operating modes and changing parameters. The user interface 38 may also include one or more inputs and associated input devices, such as a button, touchscreen, keyboard, or other device enabling a user of the device to interact with the system 10.

Figure 2:
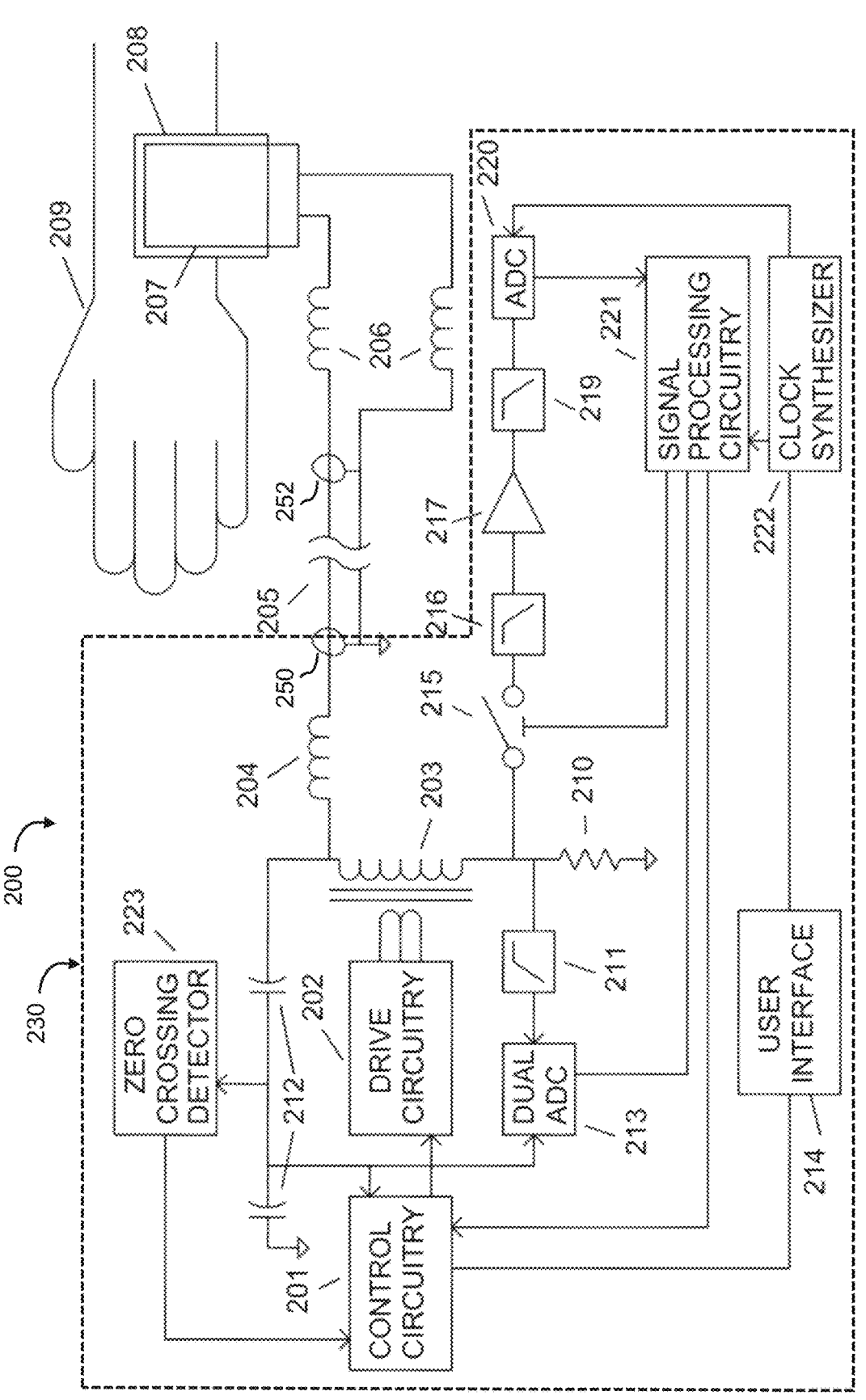
FIG. 2 is a schematic diagram of another example system for non-thermal plasma generation and putative energy detection and analysis in accordance with the disclosure.

FIG. 2 shows another example embodiment of a non-thermal plasma device 200 that uses a single cable 205 between the controller 230 and the array 207, and is used to detect a single feedback frequency. Control circuitry 201 sends signals to the drive circuitry 202 to drive a transformer 203 at a frequency that resonates with the plasma array 207. In some embodiments, the transformer 203 may be a planar transformer, which can provide advantageous coupling between the primary and secondary windings since there are only 2 turns on the primary. It also allows good repeatability since the turns of the transformer are fabricated and interconnected using an automated process. Because of the high voltage and frequency, the insulation thickness and turn spacing in the transformer 203 preferably conforms to high tolerances. Inductors 204 and 206 help reduce EMI on cable 205, which connects to an input/output terminal 250 of the controller 230 and drive/ground terminals 252 of the array 207. The plasma array 207 generates plasma through dielectric barrier discharge, and insulating sleeve 208 isolates the plasma discharge from the patient 209. The device 200 may further include a user interface 214 and signal processing circuitry 221 as described above.

Current through sense resistor 210 is connected to a high pass filter 211 and analog to digital converter (ADC) 213 to digitize the plasma current at 256 times the plasma frequency. The ADC 213 also digitizes the plasma voltage through capacitive voltage divider 212. This is used to calculate average power into the plasma array by performing a 256 point complex Fast Fourier Transform (FFT). The real power in each FFT result is corrected for loss in the high pass filter 211, and summed to calculate real power.

Sense resistor 210 is also connected to a gating circuit 215, to be sampled during a particular polarity of the plasma discharge, as the signal is only on one polarity. The gating circuit 215 may be controlled (i.e., opened and closed at a sampling rate) by signal processing circuitry 221. An output of the gating circuit 215 is connected to a low pass filter 216 and low noise amplifier 217 to pass low frequencies at 500 Hz or below while rejecting the plasma frequency. The signal is then filtered by anti-aliasing filter 219 and digitized by an ADC 220 at the plasma frequency. In a typical embodiment, filter 219 and ADC 220 are combined in an audio ADC. If the plasma frequency is precisely tuned, preferably with a fractional-N frequency synthesizer 222, the plasma can function as a harmonic mixing mechanism. This can convert a single VHF or UHF signal to a low frequency IF signal in the 300 Hz range. If the VHF/UHF signal is present, the signal processing circuitry 221 can detect the signal in the output of the ADC 220—that is, the frequency conversion performed by the wideband receiver of the device 10 in FIG. 1 now occurs in the plasma discharge instead. The IF signal is the same frequency, and the data rate at the plasma frequency is fractionally decimated to the plasma modulation frequency and analyzed by signal processing circuitry 221 and/or control circuitry 201 in the same way as in the wideband receiver of FIG. 1.

FIGS. 3A-D illustrate a non-thermal plasma emitter array 100, such as the array 11 of FIG. 1 or the array 207 of FIG. 2. An array 100 comprises a plurality of non-thermal plasma emitters 107, disposed on a rigid or flexible substrate 102 having at least two opposing surfaces, referred to herein sometimes as a top and bottom for convenience. The emitters 107 are arranged such that when the array 100 is connected to a voltage source the emitters generate a plurality of plasma plumes. The conductive plasma wave creates reactive species including ozone and nitric oxide.

A plurality of through-holes 118 are made in the substrate 102. A through-hole 118 helps reduce the array capacitance and is a ventilation hole for a fluid to flow between a first electrode 108 and a second electrode 110. Such fluids include oxygen, helium, nitrogen, sulfur hexafluoride, carbon dioxide, air, and other gases. In the preferred embodiment, the fluid is air at ambient pressure, about 1 atmosphere. The oxygen in the air is ionized by the plasma generated by the emitters 107, creating ozone. The through-holes 118 are made by drilling, etching, cutting, laser cutting, punching, or other method. In certain embodiments a through-hole is lined with a structure that directs the fluid to each electrode such as a pipe, tube, channel, or the like. A through-hole 118 can be circular, rectangular, triangular, trapezoidal, hexagonal, or other shape.

The electrically interconnected emitters 107 comprise a first electrode 110 disposed on a first side of the substrate 102, with each electrode 110 centered over one through-hole 118 in the substrate 102, and a second electrode 108 disposed on the second, opposing side of the substrate 102 and also centered over one through-hole 118 in the substrate 102. The resulting structure of a through-hole, a ground electrode, and a drive electrode comprises a plasma emitter 107. Each pair of electrodes 108, 110 can be generally centered on a through-hole 118, as shown, but in certain embodiments it may be off-center. Each electrode 108, 110 shape is preferably symmetric around the through-hole 118, such as a hexagon, circle, triangle, rectangle, square, or other shape, but in certain embodiments can be asymmetric.

A conductive drive track 112 on one side of the substrate 102 is connected to the corresponding electrodes, and a conductive ground track 104 on the opposing side of the substrate 102 is connected to the corresponding electrodes. The conductive tracks may be used to interconnect as many of the corresponding electrodes together as desired. Emitters 107 may be connected in series or in parallel, and preferably in parallel for a lower driving voltage. A drive terminal 111 is connected to the drive track 112 and a ground terminal 106 is connected to the ground track 104.

The substrate 102 is made of a dielectric material such as alumina, polycarbonate, polyimide, polyester, polytetrafluoroethylene-infused woven glass cloth, polypropylene, glass-reinforced epoxy laminate sheets, or the like. In certain embodiments a substrate has more than one layer, and the layers may be made of different materials. The substrate 102 is made of a rigid or a flexible material that can be made to conform to varying surface topography and shapes such as a rough surface, a textured surface, a smooth surface. The substrate can be two-dimensional, such as a square, curved, rectangular, round, or hexagonal. It can also be three-dimensional such as curved, cubic, tubular, or spherical. The substrate may also have a non-uniform shape or a non-symmetric shape. Substrates of rigid materials may be shaped to the desired conformation before or after the plasma emitters are made therein. Substrates of flexible materials are typically conformed to the desired shape after the array is manufactured. In a preferred embodiment, the substrate is made of thin FR-4. At a thickness of about 0.2 mm, the substrate made of FR-4 is somewhat flexible. As an alternative, the array can be fabricated from more flexible material such as polyimide film or PTFE infused fiberglass. An insulative layer 304 can be attached to the substrate 102, under the ground terminal 106 and drive terminal 111. The insulative layer 304 can be neoprene, polymer coating, Mylar®, Teflon®, or the like.

Figure 3A:
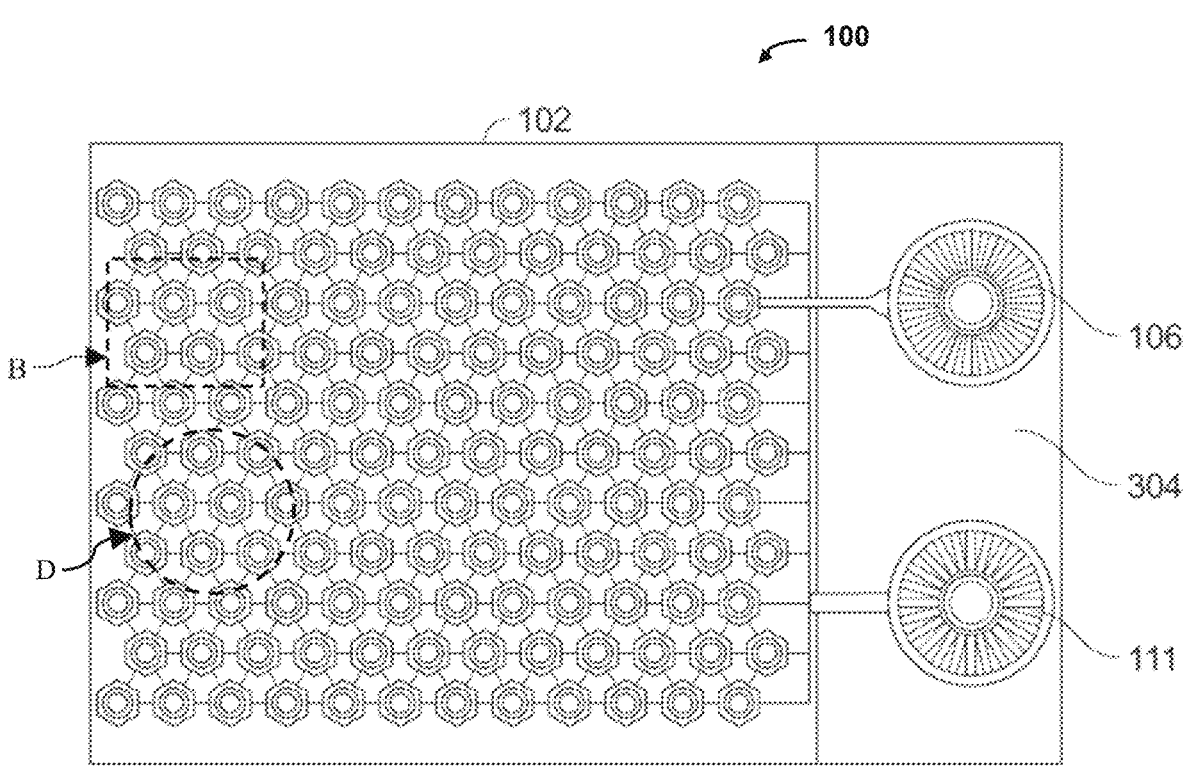
FIG. 3A is a top view of an example plasma emitter array in accordance with the disclosure.
Figure 3B:
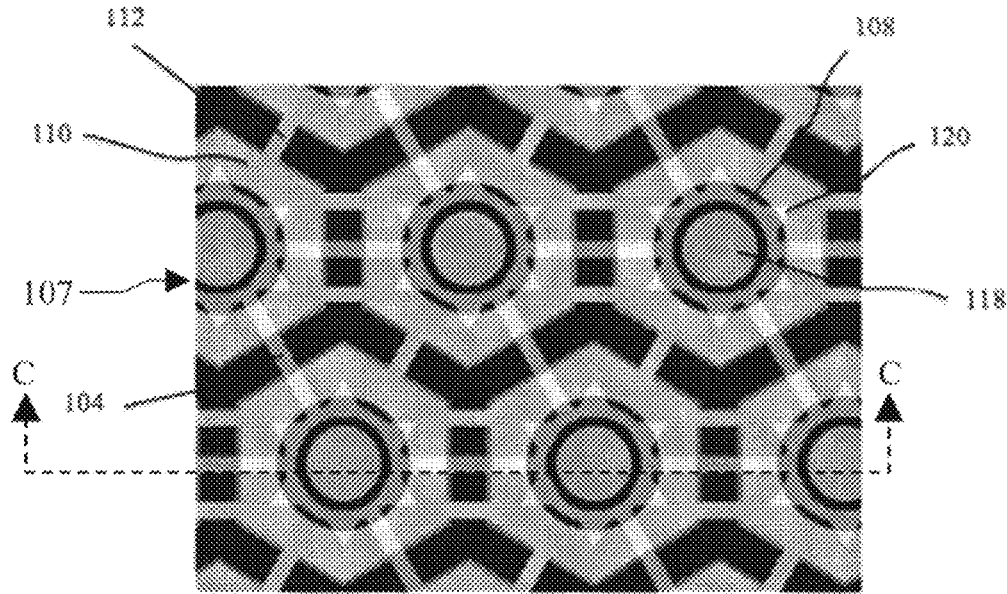
FIG. 3B is a close-up top view of the example plasma emitter array taken from Inset B of FIG. 3A.
Figure 3C:
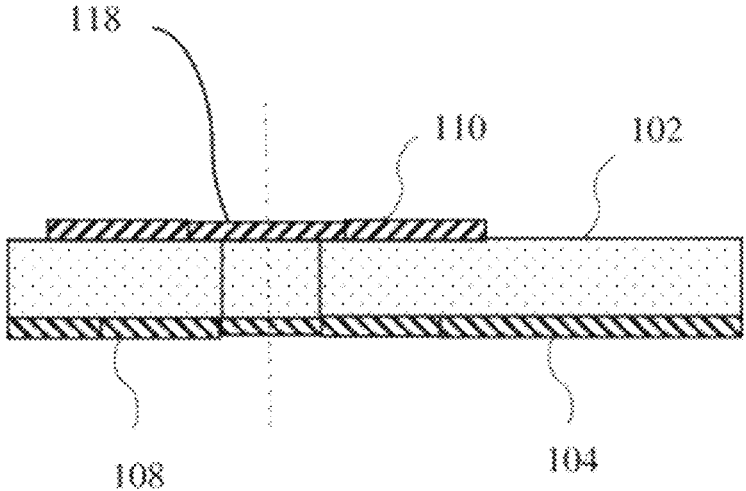
FIG. 3C is a cross-sectional side view of the plasma emitter array of FIG. 3A taken along line C-C of FIG. 3B.
Figure 3D:
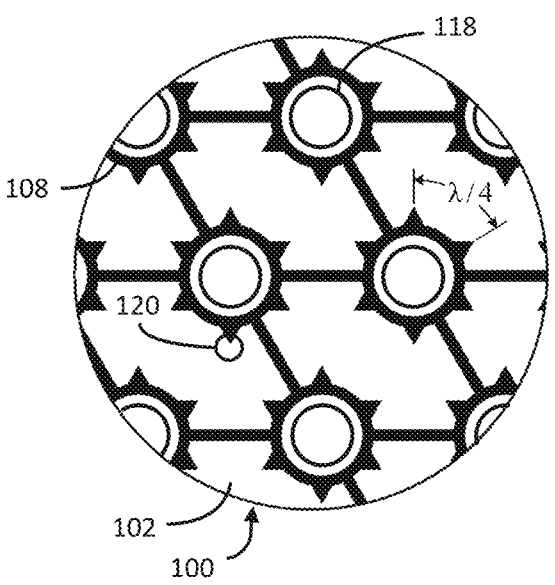
FIG. 3D is a close-up bottom view of the example plasma emitter array taken from Inset D of FIG. 3A.

Within each emitter 107, a first electrode 110 is capacitively coupled to a second electrode 108 through the dielectric substrate 102 such that when a high-enough voltage is applied, the surrounding fluid is ionized and a plasma is created, causing electrons to flow between drive and ground electrodes. In an embodiment, one of the electrodes 108, 110 comprises a sharp point 120 where the plasma is generated, since this is used to help initiate the plasma. The sharp points may take any form, such as a sharp point, a blunt point, a spear point a radius, or the like. FIG. 3D illustrates an embodiment in which the ground electrode 108 is a star with six sharp points 120.

Using mass manufacturing techniques, the cost of making the arrays is small enough that the arrays can be considered consumable or disposable, simply thrown away or recycled after one or a few uses. Any polymer in the array is consumed by the oxygen plasma, in a process commonly known as ashing. This erosion process can be slowed by adding a thin layer of glass on top of the entire array. A sol-gel process can be used to deposit thick layer, on the order of about a 100 nm. A thinner crystalline layer of $SiO_2$, $Al_2O_3$ or $Y_2O_3$ works too, and may be deposited by atomic layer deposition or plasma assisted atomic layer deposition, optionally after array burn-in for uniform plasma.

Theory of Healing

As explained above, a putative energy field or vital field is the biophysical manifestation of the concept of "life force," also known as qi, ki, chi, mana, prana, mitogenic radiation, biofield, etc. Theoretically, this "energy" operates across causal time rather than within it, giving it different properties than traditional energy forms such as thermal, optical, and mechanical; quantum entanglement in emergent time may provide the physical basis for the production of putative energy. Water, or more specifically the $H_2O$ molecule, is most likely an enabler of quantum effects, and may use the quantum vacuum as an information storage mechanism. Correspondingly, putative energy or "life force" is part of an information field, and the creation and use of the life force seems to involve conservation of information.

Oxygen is paramagnetic, meaning that it has a magnetic moment. The interaction of the magnetic moment with oxygen nuclei causes hyperfine resonances. The resonant frequencies of low-pressure oxygen are measurable with electromagnetic devices; they have been well characterized and are available at hitran.org. When the pressure applied to the oxygen is increased, the resonance becomes less distinct as molecules are bumping into adjacent molecules. When the energetic coupling into the $O_2$ molecule relies on quantum entanglement rather than magnetism, this degradation of resonant quality does not occur: quantum entanglement in emergent time allows an electron of a given spin state to be coupled to an electron of opposite spin state, but not necessarily in the same moment of time. The electron spin precesses around the direction of energy flow; this allows high quality molecular resonance to occur in the oxygen even when the oxygen is being used in a biochemical process, enabling the production of the biological torsion wave.

Specifically, the biological torsion wave is produced by the electron transport chain during oxidative phosphorylation in the mitochondria of the cell. The inner mitochondrial membrane through which the electron transport occurs is composed of amino acids. The molecular structure of amino acids is chiral, which imposes a spin coupling between surrounding $O_2$ molecules. The biological torsion wave takes the form of a time varying and spinning electromagnetic potential. Electromagnetic fields are not generated by the electronic transport chain, but externally applied fields such as radio waves can interact with the biological torsion wave and influence the organism: because the waves are spinning, they influence electron spin in materials through spin-spin interaction. In torsion wave research, the energy is usually generated by a physically moving magnetic field, and the plasma discharge creates such a mechanism. This mechanism converts the quantum torsion waves into electromagnetic waves, and vice-versa, through spin-spin interaction. At the same time, the collapsing magnetic field along the plasma wave creates a zone of population inversion.

Plasma array 100 comprises an array of plasma emitters, each having a pair of electrodes 108, 110 patterned on a thin PCB or other suitable substrate. The array 100, as energized by the controller described herein, uses dielectric barrier discharge to generate an air plasma. The first electrode 108 may comprise a conductive metal ring 109 (encircling a through-hole 118 in some embodiments) and a plurality of projections 119 extending outward from the ring 109 along the surface of the substrate 102 and tapering to sharp metal points 120. The plasma originates in plumes from the points 120 of the first electrode 108, forming a plasma wave that radiates outward from the points 120 over the course of about 1.5 ns. The plasma wave propagates at about 500 km per second. This plasma wave is a physically moving conductor, and a convertor between torsion waves and electromagnetic waves. The points 120 may be distributed uniformly around the rings 109 with a spacing of either a quarter wavelength ($\lambda/4$, as shown in FIG. 3D) or a half wavelength ($\lambda/2$). This makes the rings 109 and array 100 resonate at around 60 GHz, within the frequency band of many $O_2$ hyperfine resonances. At 118.75 GHz, oxygen resonance J(1,0), the array 100 resonance is even better defined. Because of the high quality of the oxygen resonances in the quantum domain, the tiny individual signals generated by each reaction mutually injection-lock and form a stronger signal. When analyzed by the present controller in constant time, the signals take the form of exponential frequency chirps around each oxygen resonant frequency.

Thus, the array 100 is placed in the vital field of the subject (as shown in FIGS. 1 and 2) and activated to begin generating plasma. The array 100 amplifies the vital field and reflects the amplified field back onto the subject as follows:

the moving plasma wave converts torsion energy to electromagnetic energy;

the moving plasma wave also creates a collapsing magnetic field to create a zone of population inversion;

the electromagnetic energy resonates in the metal rings 109 of the array;

the resonant electromagnetic energy is amplified by the population inversion from the oxygen plasma; and the moving plasma wave converts electromagnetic energy to torsion energy. This energy interacts with mitochondrial and nuclear DNA and is used to help guide the cell during mitosis as an error correcting mechanism. The reflected and amplified biological torsion wave also flips electron spins in the body. Since the spin-down electron contains more energy than the spin-up electron, the spin will tend to flip back to conserve energy. When the spin flips back, there is a slight probability for a photon to be released. This phenomenon has been observed as biophotons.

The controller (e.g., controller 50 of FIG. 1 or controller 230 of FIG. 2) starts and stops the supply of power to the array at a specified rate, modulating the production of plasma at a "plasma frequency," and this plasma frequency influences how well the plasma works to treat a particular condition. The modulation enhances the coherence of emergent-time quantum entanglement, producing an enhanced healing effect extending inches below the skin or under the skull. The plasma also creates active oxygen and nitrogen species which can have an anti-bacterial or anti-fungal effect at and approximate the surface of the skin.

Theory of Putative Energy and Vital Field Detection and Analysis

The present systems and devices detect, within an input signal, interactions of the cold plasma discharge with the vital field of the subject in the area approximate the plasma array. Example embodiments described below operate in accordance with one or more of several theories of putative energy interaction that is detectable via signal analysis. Furthermore, the described signal processing techniques enable extraction, from the input signal, a signature representing the vital field; methods described herein include processing the signature to identify (and, in turn, diagnose) physical conditions and other biological characteristics, such as pain, illness, and the presence of pathogens and/or damaged cells.

A plasma array as described herein may comprise an array of plasma emitters patterned on a PCB or other substrate, having circular electrodes with the drive electrode being ringed with conductive sharp points as described herein; the pattern of emitters resonates in the 60 GHz range. In one proposed manner of operation, this resonance during cold plasma production causes energetic interactions of the cold plasma with the putative energy in the vital field, at hyperfine resonances of oxygen; this converts the putative energy in the "information field" into electromagnetic energy as described above with respect to the theory of healing. The present device 200 may detect and analyze this electromagnetic energy.

Since the cold plasma discharge is a non-linear process, it creates a frequency mixing mechanism. There are many spectral lines of oxygen, and some of these can produce frequency mixing products, i.e., electromagnetic waves in the VHF and UHF frequency range. These mixing products impinge upon a wideband receiver of the present device.

In an embodiment, the ASIC may be implemented in a 16 nm FinFET process. This would allow efficient power usage for the ADC, clock synthesizer and high speed digital circuitry, and permit sufficient memory within a total die size of about 4 mm square or less. This process would allow the fabrication of a system on a chip (SOC) along with external flash memory and sufficient drive voltage for gate drivers. A 22 nm FDSOI process could be an alternative, allowing non-volatile memory on chip.

Since a relatively small number of signal peaks are needed for data analysis, the data can be analyzed on the ASIC, or streamed over a USB or wireless connection. In certain configurations, the plasma array may also act as a radio antenna. The system in the present disclosure includes a plasma feedback radio receiver device. When the plasma array is operated away from the body of a living organism the radio receiver device is able to collect data about the ambient environment. Collected results may be stored in a database connected to the system. Data from the database may be used to calibrate the plasma array for use with living organism. The stored results in the database may be used to differentiate ambient environmental radio signals from biofield signals generated by a living organism when the plasma array is operated next to the body.

Tuning

Referring again to FIG. 2, transformer 203 and array 207, connected in parallel, form a resonant, parallel LC circuit with an inherent capacitance that may cause variations in the drive frequency. In some embodiments, a coaxial cable 205 connects transformer 203 to plasma array 207. Since the plasma array 207 acts as a wideband noise generator, inductors 206, such as ferrite beads, may be electrically coupled to the electrical path between each terminal of the array 207 and the corresponding conductor of the cable 205 to reduce the unintended effectiveness of the cable 205 as an antenna. The cable 205 may also be coupled at one or both ends to connectors (not shown) that removably connect to the controller and to the array 207, respectively; the cable 205 and any connectors may also have an inherent capacitance affecting the resonance of the transformer-array circuit— that is, the separate inherent capacitances of the array 207, cable 205 and its connectors, and transformer 203, may be summed into a combined capacitance that determines the resonant frequency of the LC circuit.

The controller including the control circuitry 201 and the drive circuitry 202 finds the resonant frequency of the transformer-array combination and then drives the transformer 203 at the corresponding drive frequency. This allows the transformer primary switching to be interrupted much faster than for a self-oscillating converter (which by nature would not require tuning). DC power is supplied to the transformer by means of a buck converter circuit. In one embodiment, the transformer needs about 7V when generating plasma. The buck converter supplies it from 12V. The PWM signal for the converter has a small duty cycle during tuning to produce a low test current for tuning.

A zero crossing detector 223 measures the phase of the output voltage from transformer 203, producing a (digital) phase waveform that is fed back to the control circuitry 201 and used to keep the drive frequency matched to the resonant frequency of the array 207, through the parallel LC circuit. The controller tunes the transformer 203 by sweeping its frequency over the operating frequency range. When the frequency is near resonance, the zero-crossing signal will no longer be a DC level—it will be a digital signal whose phase with respect to the driving signal depends on which side of resonance the drive signal is on. When the transformer is in resonance, the zero-crossing signal is in phase with the drive signal. At that point, the controller is finished with the tuning process.

Contamination and Rapid Shutdown

The next step after tuning is to apply power to the array 207. Since there is a possibility of a bad connection or failing array, the power is ramped up slowly to allow detection of arcing faults. The zero-crossing phase is monitored as the buck converter PWM duty cycle is increased to make sure there are no sudden jumps. A control loop slowly adjusts the frequency of the transformer 203 to keep the zero-crossing centered. This compensates for frequency drift due to temperature changes in the transformer 203 and array 207.

The zero-crossing signal can be monitored to provide instant shutdown in the event of a fault such as electric shock or arcing. The phase relationship is most sensitive at resonance. A rapid shift signals something going wrong. The transformer 203 is always running; even with the modulation "off," the transformer 203 is running but at a lower voltage. The controller can respond within one or two cycles to limit electric shock duration to 40 microsecs. If the zero-crossing phase makes a sudden jump outside of a permissible window, the controller shuts down the drive. This happens when the array 207 dielectric breaks down at end-of-life, the connection to the array 207 is interrupted, or the user touches an exposed surface of the array 207. This safety interlock can respond very quickly. It can shut off the array 207 within one transformer 203 cycle by interrupting the switching on the transformer 203 primary. This protects uninformed users against shocks from misuse.

If the array 207 is contaminated, the surface conductivity will lower the Q of the transformer-array resonant circuit to the point that the zero-crossing signal is not seen. The user will be prompted to clean the array 207. The usual source of contamination is reactive nitrogen species combining with humidity in the air to form nitric acid, which is easy to wash off with water.

Thus, in various non-limiting examples, embodiments, configurations, and/or implementations, the present disclosure provides a device for detecting and analyzing vital fields, the device including: a dielectric barrier discharge array fabricated on a thin substrate with low dielectric loss; an air permeable sheet for electrical insulation from the skin; a transformer for generating sufficient AC voltage to cause air breakdown in the array; a signal transformer and bypass capacitor for isolating the radio frequency current from the plasma discharge; circuitry for amplification and narrow-band spectrum analysis of the plasma discharge current. The amplified signal from the plasma discharge current is gated to include only signal from the part of the drive waveform where plasma discharge predominantly occurs. A Fast Fourier Transform (FFT) is used to reduce the complexity of frequency conversion; the relevant (about 1 out of 500) FFT results are fractional decimated to output Intermediate Frequency (IF) signals at a sample rate matching the plasma modulation rate. The IF signals are analyzed to aid the user with the correct array placement on the body, and the detection of medical conditions.

The drive control for the high voltage transformer can be integrated into an Application Specific Integrated Circuit (ASIC), along with the signal analysis circuitry and an associated Central Processing Unit (CPU) for real-time analysis. The ASIC is connected to a Bluetooth transceiver for the purpose of using a smart phone as a secondary user interface. The ASIC can consist of narrow-band spectrum analysis circuitry and an associated Central Processing Unit (CPU) for real-time analysis, and the plasma control is performed by a separate micro-controller; the plasma is modulated by turning it on and off at a set frequency and duty cycle. The plasma modulation frequency can be set to address the treatment of a specific physical condition. Power absorbed in the plasma array can be measured and used by the controller to find an optimum modulation frequency; the measured power is used to provide feedback to the user. Radio signals in the VHF and UHF frequency ranges, generated by plasma array interaction with the body, can be detected and analyzed for the purpose of adjusting the modulation frequency, and providing feedback to the user.

In another aspect, described herein is a non-thermal plasma generation device including a capacitance dielectric discharge array and a controller electrically connectable to the array. The array includes a dielectric substrate and a plurality of electrically interconnected plasma emitters each having a first electrode and a second electrode. In each of the plurality of plasma emitters, the corresponding first electrode may include a metal ring and a plurality of metal projections spaced about a perimeter of the metal ring, each of the plurality of projections terminating in a corresponding sharp point that resonates at the resonant frequency to emit a plume of the non-thermal plasma. The controller includes: a transformer that receives an electric current and generates sufficient AC voltage to cause the plurality of plasma emitters to ionize surrounding air and produce the non-thermal plasma; and, drive circuitry in electrical communication with the transformer, the drive circuitry configured to drive the transformer at a resonant frequency of about 60 GHz and multiples thereof when the transformer is applying the AC voltage to the array.

The dielectric substrate may be a silica- or ceramic-loaded polymer to allow flexibility but resist plasma erosion. The polymer may be polytetrafluoroethylene. The device may further include at least one coaxial cable electrically connecting the array to the controller. The controller may further include one or more inductors electrically connected between the transformer and the at least one coaxial cable to reduce signal reflections on the at least one coaxial cable.

The controller may further include control circuitry electrically connected to the drive circuitry, the control circuitry modulating the non-thermal plasma at a plasma modulation frequency by controlling the drive circuitry to energize and de-energize the transformer at the plasma modulation frequency and with a duty cycle. The control circuitry modulates the non-thermal plasma by causing the drive circuitry to modulate a voltage on a primary winding of the transformer based on an arbitrary waveform instead of a fixed tone. The plasma modulation frequency may correspond to an application of the non-thermal plasma for therapeutic treatment of a specific physical condition. Generation of the non-thermal plasma in proximity to a subject's skin causes reverse power in the array, and the controller may be configured to measure a signal in the reverse power and adjust the plasma modulation frequency to an optimum frequency in response to a measurement of the signal. The controller may further include a user interface in electronic communication with the control circuitry, and the measurement of the signal may be used to provide feedback to a user of the device via the user interface.

The controller may further include signal processing circuitry in electronic communication with the control circuitry, the signal processing circuitry configured to detect radio signals, in the VHF and UHF frequency ranges, generated by interaction of the non-thermal plasma with a subject's body, the control circuitry receiving, from the signal processing circuitry, information associated with the radio signals and adjusting the modulation frequency based on the information. The control circuitry and the drive circuitry may be integrated into an Application Specific Integrated Circuit (ASIC) along with the signal analysis circuitry and an associated Central Processing Unit (CPU) for real-time analysis of the radio signals. Or, the controller may be an Application Specific Integrated Circuit (ASIC) integrating the signal analysis circuitry and an associated Central Processing Unit (CPU) for real-time analysis of the radio signals, and the control circuitry comprises a micro-controller that is separate from the ASIC.

The controller may include a frequency synthesizer electrically connected to the signal processing circuitry; the signal processing circuitry, using a tuned output of the frequency synthesizer as a plasma frequency, mixes a harmonic of the plasma frequency with a secondary mixing product of O2 hyperfine resonances in the VHF or UHF range, the secondary mixing product being present in the radio signals, to generate an array current for analysis below the plasma modulation frequency. The signal processing circuitry and the control circuitry may cooperate to analyze the array current for feedback and medical diagnostic purposes.

The controller may include means for detecting excess array current and stopping the modulation of the electric current to the transformer when the excess array current is detected. The control circuitry may be configured to monitor harmonics of current and voltage on the transformer secondary winding, and to use the harmonics to compute real time average power into the array. The device may further include a coaxial cable removably connected to the array and to the controller, and cooperating with the transformer and the array to form a wideband receiver that receives frequency mixing products produced by the plasma. The controller may further include memory storing computer instructions and one or more microcontrollers, one or more application-specific integrated circuits (ASICs), or a combination of microcontrollers and ASICs, in electronic communication with the memory and cooperating to execute the computer instructions to: sample, at a sampling rate corresponding to a first polarity of the plasma's discharge, an input from the wideband receiver to obtain an input signal; process the input signal to extract the frequency mixing products; amplify and digitize VHF and UHF signals in the frequency mixing products; analyze the VHF and UHF signals to determine whether a signature corresponding to a vital field is present; and, responsive to determining that the signature is present, generate feedback associated with the vital field.

While there has been illustrated and described what is at present considered to be the preferred embodiments of the present invention, it will be understood by those skilled in the art that various changes and modifications may be made and equivalents may be substituted for elements thereof without departing from the true scope of the invention. The embodiments of the invention described herein are not intended to be exhaustive or to limit the invention to precise forms disclosed. Rather, the embodiments selected for description have been chosen to enable one skilled in the art to practice the invention. Therefore, it is intended that this invention not be limited to the particular embodiments disclosed, but that the invention includes all embodiments falling within the scope of the appended claims.

What is claimed is:

1. A non-thermal plasma generation device comprising:
a capacitance dielectric discharge array comprising a dielectric substrate and a plurality of electrically interconnected plasma emitters each comprising a first electrode and a second electrode; and
a controller electrically connectable to the array, the controller comprising:
a transformer that receives at a primary winding of the transformer a first signal having an electric current and generates sufficient AC voltage to cause the plurality of plasma emitters to ionize surrounding air and produce the non-thermal plasma; and
drive circuitry in electrical communication with the transformer, the drive circuitry configured to drive the transformer with a second signal having a frequency at a resonant frequency of about 60 GHz and multiples thereof when the transformer is applying the AC voltage to the array.

2. The device of claim 1, wherein in each of the plurality of plasma emitters, the corresponding first electrode comprises a metal ring and a plurality of metal projections spaced about a perimeter of the metal ring, each of the plurality of projections terminating in a corresponding sharp point that resonates at the resonant frequency to emit a plume of the non-thermal plasma.

3. The device of claim 1, wherein the dielectric substrate comprises a silica- or ceramic-loaded polymer to allow flexibility but resist plasma erosion.

4. The device of claim 3, wherein the polymer comprises polytetrafluoroethylene.

5. The device of claim 1, further comprising at least one coaxial cable electrically connecting the array to the controller.

6. The device of claim 5, wherein the controller further comprises one or more inductors electrically connected between the transformer and the at least one coaxial cable to reduce signal reflections on the at least one coaxial cable.

7. The device of claim 1, wherein the controller further comprises control circuitry electrically connected to the drive circuitry, the control circuitry modulating the non-thermal plasma at a plasma modulation frequency by controlling the drive circuitry to energize and de-energize the transformer at the plasma modulation frequency and with a duty cycle.

8. The device of claim 7, wherein the control circuitry modulates the non-thermal plasma by causing the drive circuitry to modulate a voltage on a primary winding of the transformer based on an arbitrary waveform instead of a fixed tone.

9. The device of claim 7, wherein the plasma modulation frequency corresponds to an application of the non-thermal plasma for therapeutic treatment of a specific physical condition.

10. The device of claim 7, wherein generation of the non-thermal plasma in proximity to a subject's skin causes reverse power in the array, and wherein the controller is configured to measure a signal in the reverse power and adjust the plasma modulation frequency to an optimum frequency in response to a measurement of the signal.

11. The device of claim 10, wherein the controller further comprises a user interface in electronic communication with the control circuitry, and wherein the measurement of the signal is used to provide feedback to a user of the device via the user interface.

12. The device of claim 7, wherein the controller further comprises signal processing circuitry in electronic communication with the control circuitry, the signal processing circuitry configured to detect radio signals, in the VHF and UHF frequency ranges, generated by interaction of the non-thermal plasma with a subject's body, the control circuitry receiving, from the signal processing circuitry, information associated with the radio signals and adjusting the modulation frequency based on the information.

13. The device of claim 12, wherein the control circuitry and the drive circuitry are integrated into an Application Specific Integrated Circuit (ASIC) along with the signal analysis circuitry and an associated Central Processing Unit (CPU) for real-time analysis of the radio signals.

14. The device of claim 12, wherein the controller comprises an Application Specific Integrated Circuit (ASIC) integrating the signal processing circuitry and an associated Central Processing Unit (CPU) for real-time analysis of the radio signals, and the control circuitry comprises a micro-controller that is separate from the ASIC.

15. The device of claim 12, wherein the controller further comprises a frequency synthesizer electrically connected to the signal processing circuitry, and wherein the signal processing circuitry, using a tuned output of the frequency synthesizer as a plasma frequency, mixes a harmonic of the plasma frequency with a secondary mixing product of O2 hyperfine resonances in the VHF or UHF range, the secondary mixing product being present in the radio signals, to generate an array current for analysis below the plasma modulation frequency.

16. The device of claim 15, wherein the signal processing circuitry and the control circuitry cooperate to analyze the array current for feedback and medical diagnostic purposes.

17. The device of claim 7, wherein the controller further comprises means for detecting excess array current and stopping the modulation of the electric current to the transformer when the excess array current is detected.

18. The device of claim 7, wherein the control circuitry is configured to monitor harmonics of current and voltage on the transformer secondary winding, and to use the harmonics to compute real time average power into the array.

19. The device of claim 1, further comprising a coaxial cable removably connected to the array and to the controller, and cooperating with the transformer and the array to form a wideband receiver that receives frequency mixing products produced by the plasma.

20. The device of claim 19, wherein the controller further comprises memory storing computer instructions and one or more microcontrollers, one or more application-specific integrated circuits (ASICs), or a combination of microcontrollers and ASICs, in electronic communication with the memory and cooperating to execute the computer instructions to:

sample, at a sampling rate corresponding to a first polarity of the plasma's discharge, an input from the wideband receiver to obtain an input signal;

process the input signal to extract the frequency mixing products;

amplify and digitize VHF and UHF signals in the frequency mixing products;

analyze the VHF and UHF signals to determine whether a signature corresponding to a vital field is present; and responsive to determining that the signature is present, generate feedback associated with the vital field.

\* \* \* \* \*